(12) United States Patent
Van Vlimmeren

(10) Patent No.: US 8,566,738 B2
(45) Date of Patent: Oct. 22, 2013

(54) SYSTEM FOR COLLECTING DATA ELEMENTS RELATING TO EVENTS OF INTERVENTIONAL PROCEDURE

(75) Inventor: Ineke Cornelia Francisca Van Vlimmeren, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 434 days.

(21) Appl. No.: 12/742,946

(22) PCT Filed: Nov. 17, 2008

(86) PCT No.: PCT/IB2008/054799
§ 371 (c)(1),
(2), (4) Date: May 14, 2010

(87) PCT Pub. No.: WO2009/066222
PCT Pub. Date: May 28, 2009

(65) Prior Publication Data
US 2011/0167373 A1 Jul. 7, 2011

(30) Foreign Application Priority Data

Nov. 19, 2007 (EP) .................................. 07120981
Apr. 7, 2008 (EP) .................................. 08154148

(51) Int. Cl.
*G06F 3/048* (2013.01)
*A61B 5/05* (2006.01)
*A61N 1/00* (2006.01)

(52) U.S. Cl.
USPC ............ 715/772; 600/425; 600/427; 607/122

(58) Field of Classification Search
USPC ........... 715/771, 772; 705/2, 3; 382/131, 132; 600/425, 427; 607/122
See application file for complete search history.

(56) References Cited

U.S. PATENT DOCUMENTS 6,188,407 B1* 2/2001 Smith et al. ................... 715/841
6,332,147 B1* 12/2001 Moran et al. .................. 715/203
6,675,044 B2* 1/2004 Chen ............................... 607/30
7,757,183 B2* 7/2010 Rutledge et al. .............. 715/781
(Continued)

FOREIGN PATENT DOCUMENTS

WO 2007066312 A1 6/2007

OTHER PUBLICATIONS

IEEE 100, The Authoritative Dictionary of IEEE Standards Terms, 7th edition, copyright 2000 by The Institute of Electrical and Electronics Engineers. ISBN 0-7381-2601-2. p. 398.*

(Continued)

*Primary Examiner* — Steven Sax
*Assistant Examiner* — Wilson Varga

(57) ABSTRACT

A system for collecting data elements relating to events in an interventional procedure includes an input, a clock, a memory and a display. The input, during the interventional procedure, receives the data elements from at least two systems use in the interventional procedure. The clock registers a time of receipt of the data elements. The memory stores items relating to respective events, each item including the corresponding data element and the corresponding time of receipt. The display displays representations of the items sequentially along a timeline in accordance with the respective times of receipt.

11 Claims, 5 Drawing Sheets

(56) References Cited

U.S. PATENT DOCUMENTS

| | | | |
|---|---|---|---|
| 2002/0173992 A1* | 11/2002 | Dang | 705/3 |
| 2003/0065537 A1* | 4/2003 | Evans | 705/2 |
| 2005/0162384 A1* | 7/2005 | Yokoyama | 345/156 |
| 2005/0187796 A1* | 8/2005 | Rosenfeld et al. | 705/3 |
| 2006/0184160 A1 | 8/2006 | Ozaki | |
| 2006/0265249 A1* | 11/2006 | Follis et al. | 705/3 |
| 2007/0135705 A1* | 6/2007 | Lorenz et al. | 600/410 |
| 2007/0185739 A1* | 8/2007 | Ober et al. | 705/3 |
| 2008/0161658 A1 | 7/2008 | Tashiro | |
| 2008/0208631 A1* | 8/2008 | Morita et al. | 705/3 |
| 2008/0243548 A1* | 10/2008 | Cafer | 705/3 |
| 2008/0244453 A1* | 10/2008 | Cafer | 715/835 |

OTHER PUBLICATIONS

Bui et al: "Timeline:Visualizing Integrated Patient Records"; IEEE Transactions on Information Technology in Biomedicine, vol. 11, No. 4, Jul. 2007, pp. 462-473.

Van Vlimmeren, I.: "De Efo Kamer Van De Toekomst: Conceptontwikkeling Voor Een Nieuwe User-Interface in De Efo Kamer"; Dissertation for Technische Universiteit Delft and Philips Medical Systems B.V.; Jun. 2005, 128 Page Document.

Van Vlimmeren, I.: "De Efo Kamer Van De Toekomst: Conceptontwikkeling Voor Een Nieuwe User-Interface in De Efo Kamer"; Appendices of Dissertation for Tu Delft and Philips Medical Systems, Jun. 2005, 87 Page Document.

\* cited by examiner

SYSTEM FOR COLLECTING DATA ELEMENTS RELATING TO EVENTS OF INTERVENTIONAL PROCEDURE

FIELD OF THE INVENTION

This invention relates to a system for collecting data elements relating to events in an interventional procedure, the system comprising a display for displaying representations of the data elements sequentially along a timeline.

This invention further relates to a method for collecting data elements relating to events in an interventional procedure and a computer program product for performing said method.

BACKGROUND OF THE INVENTION

Interventional procedures are used for diagnosis or treatment that involve, e.g., the following:
1) Making a cut or a hole to gain access to the inside of a patient's body, for example, when carrying out an operation or inserting a tube into a blood vessel.
2) Gaining access to a body cavity, such as the digestive system, lungs, womb or bladder, without cutting into the body. Such procedures include, for example, examining or carrying out treatment on the inside of the stomach using an instrument inserted via the mouth.
3) Using electromagnetic radiation (e.g. X-rays, lasers, gamma-rays and ultraviolet light).

For such interventional procedures, e.g., interventional radiology, interventional cardiology and/or electrophysiology measurements may be used. At the moment, it is known for electrophysiological (EP) systems to save data in a log file on the recording system itself. This file contains information from, e.g., the recording system, the ablation system and the stimulator. Also medications can be added. The log file in these recording systems is a list with only text. It doesn't contain all information created during the procedure and it doesn't create a good overview; it is difficult to review data because it is all text. Different colors are used to mark different kind of events, but then still the list is very long and it takes much time to find the specific data you need.

Cardiology information systems containing a procedure log are known as well. These systems are not designed for EP procedures but for other cardiology interventions. The log file in these systems also consists of a list with text and doesn't contain much specific EP information. The information that can be saved in this log file therefore is incomplete for EP.

Reports can be created in both systems, but in both cases the reports will not contain all information needed. There is no system that combines all information of relevance into one report. Image information of X-ray systems and EP mapping systems that is acquired during an EP procedure is stored on the respective system hard disks. Sometimes there is a link between the EP mapping and the EP recording systems, but logging of events in such combined systems is not possible.

The known systems experience a number of problems. In the current EP labs a huge amount of data is created during an EP procedure by different pieces of equipment. Reviewing the data during and after the procedure is currently cumbersome as this information is saved in different ways; on systems, on disks and sometimes on the network of the hospital. Furthermore there is no time link between the different forms of data storage making it difficult to review the data in sequential order, as would be optimal to follow the subsequent procedure steps.

The disconnected data storage and resulting review on different systems make it impossible to create a good and complete EP report in an easy way.

OBJECT OF THE INVENTION

It is an object of the invention to provide a system for collecting data elements relating to events in an interventional procedure, offering a clearer and more useful overview of the relevant data concerning the interventional procedure.

SUMMARY OF THE INVENTION

According to a first aspect of the invention, this object is achieved by providing a system for collecting data elements relating to events in an interventional procedure. The system comprises an input for, during the interventional procedure, receiving the data elements from at least two systems used in the interventional procedure, a clock for registering a time of receipt of the data elements, a storage for storing items relating to respective events, each item comprising the corresponding data element and the corresponding time of receipt and a display for displaying representations of the items sequentially along a timeline in accordance with the respective times of receipt.

The main advantage of the system according to the invention is that, unlike the prior art systems, it does not only provide a collection of results from different systems and/or events. According to the invention, during the interventional procedure, relevant data is received from different systems and the time of receipt is registered. The information from different systems that needs to be stored is time stamped, e.g., using a master clock. A graphical representation of the timeline represents the time stamped information acquired during the procedure. This provides the possibility to save all information in the context of the procedure in one system and have easy access to this information. The displayed timeline provides a clear and useful overview of everything that happened during the procedure. The sequential ordering along the timeline makes it easy to observe relations between measurement values obtained by different systems. Such relations are much more difficult to observe when having to compare separate log-files of different systems, especially when the different systems use different clocks.

Instead of long lists with only text, icons and pictures may be used to create a good overview. This provides a structured overview to easily retrieve and review saved information. The system gathers information created during an interventional procedure and displays icons and text labels along an indication of time, in the context of the procedure. The system may allow easy access to the information through selecting said icons and text labels. It gives the medical staff a good overview of all the steps during the procedure and of all information created, which makes it easy to review data during and after the procedure. It will also vastly improve the ease to create a report at the end of the procedure.

According to a second aspect of the invention a method for collecting data elements relating to events in an interventional procedure is provided, the method comprising the steps of during the interventional procedure, receiving the data elements from at least two systems used in the interventional procedure, registering a time of receipt of the data elements, storing items relating to respective events, each item comprising the corresponding data element and the corresponding time of receipt and displaying representations of the items sequentially along a timeline in accordance with the respective times of receipt.

These and other aspects of the invention are apparent from and will be elucidated with reference to the embodiments described hereinafter.

DETAILED DESCRIPTION OF THE INVENTION

Figure 1:
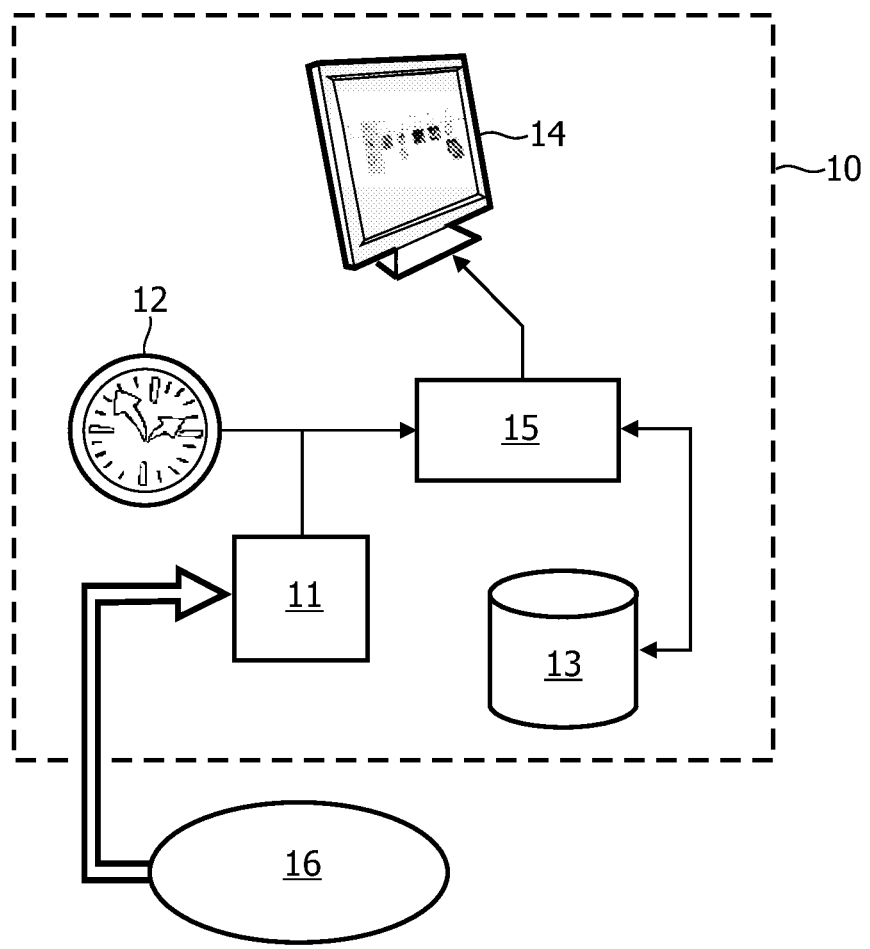
FIG. 1 schematically shows a first system according to the invention.

FIG. 1 schematically shows a first system 10 according to the invention. The invention is a computer-based and software system (henceforward called "Timeline") that keeps track of all information that is saved on the same system or other systems during an EP or other interventional procedure. During the interventional procedure, the input 11 of the system 10 receives information from one or more systems 16, used for the interventional procedure. All information to be stored gets a unique timestamp from a master clock 12. Electronic circuitry, a processor 15 or a computer, processes the incoming and time stamped data. Alternatively, the processor 15 itself provides the time stamp of the incoming information. For all relevant events relating to the interventional procedure, items (data+time stamp) are stored on storage 13, preferably in a database. The storage 13 may be a hard disk, optical disk or other suitable storage medium. The EP timeline shows a graphical display that presents all saved information as icons and/or text with the time of acquisition in sequential order. The processor 15 is arranged for displaying the timeline (see FIGS. 3-7) with information about the interventional procedure on a display 14. The timeline shows representations of relevant information concerning the interventional procedure. The timeline may be constructed from the real-time data received by the system 10, or may be generated from data stored in the storage 13. The display 14 thus is capable of showing real-time information and/or information about earlier procedures.

It is to be noted that the timeline is used during an interventional procedure and it is not merely a line with patient historical records showing results and conclusions of procedures. Collection and storage of the information is performed in real-time.

A report may be generated from the information stored in the timeline. The report may be created via a template with the possibility to manually add or delete items. This provides the possibility to create one comprehensive report in an easy way. Preferably, from the timeline, a report is created automatically via a template (template will be customizable). Besides that the snapshots from the timeline can be selected (marked) manually during the case for the report.

The timeline according to an embodiment enables the intraprocedural sequential review of relevant multimodal procedure data, obtained by separate systems 16 such as intracardiac recording, X-ray imaging, Ultrasound imaging, EP mapping systems, etc, from a single work spot, without the cumbersome need to view this data on the separate systems. Thus, a rapid review of a certain data element can be easily reviewed in the time related context of all other recorded data elements relevant to the interventional procedure.

A historical medical record of patient information may be presented as a number of data sets along a time line. Such a data set may relate to a certain procedure and may contain various data elements relating to aspects of the procedure. In an embodiment of the invention, the data elements relating to such a procedure are stored and represented themselves as pieces of information along a time line.

Figure 2:
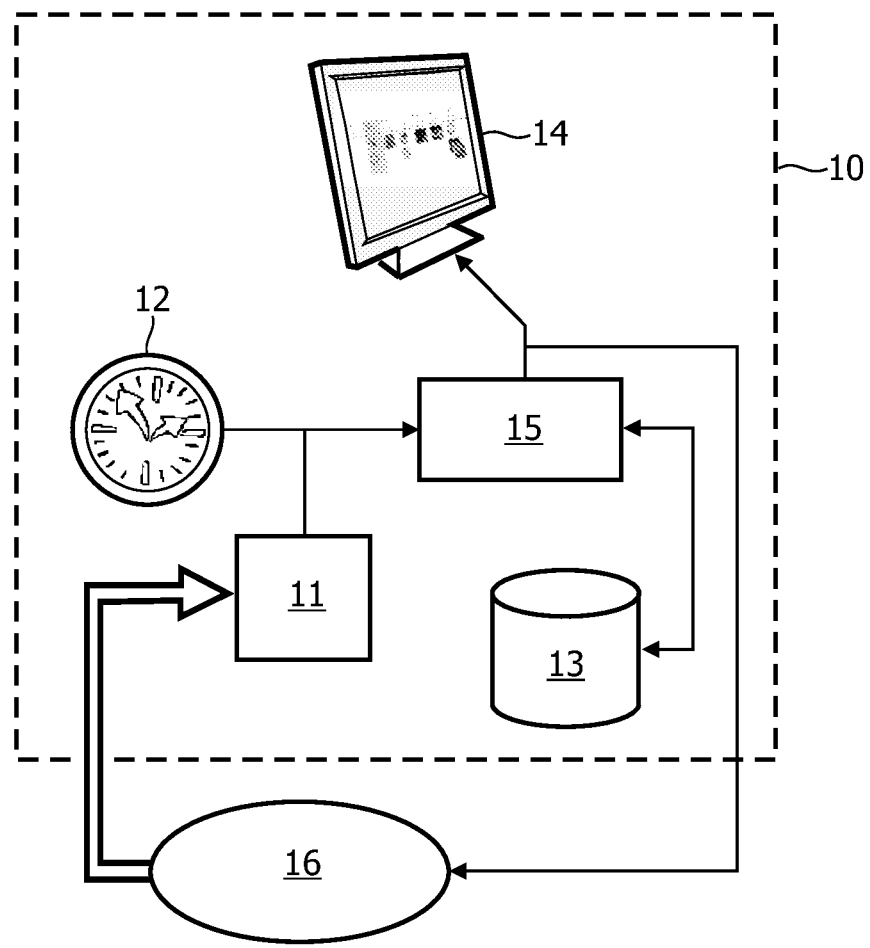
FIG. 2 schematically shows a second system according to the invention.

FIG. 2 schematically shows a second system 10 according to the invention. In this embodiment, not only the display 14 of the data collection system itself, but also the other systems 16 used for the interventional procedure are used for providing information to the user. For example, when the user clicks on data in the timeline, data coming from another system 16 (e.g. recording run) will be opened and shown on the corresponding system 16.

Figure 3:
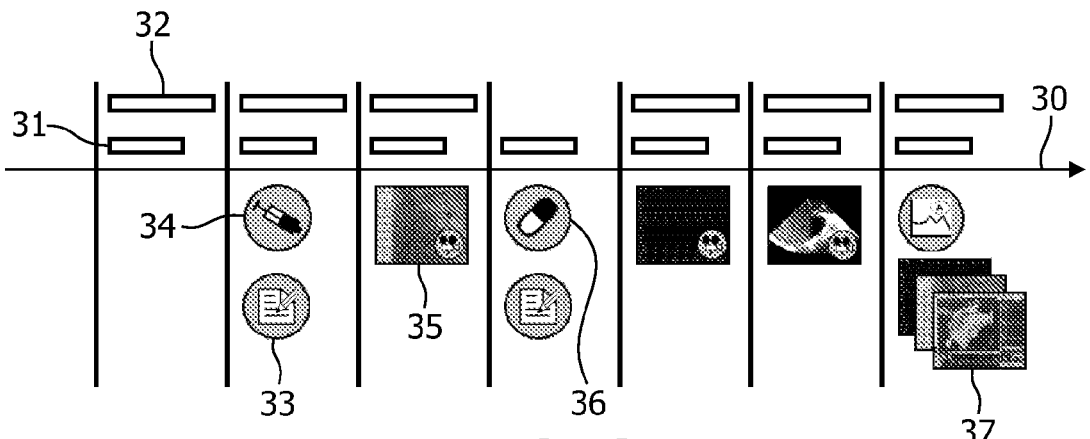
FIGS. 3-5 show exemplary timelines as may be displayed according to the invention.
Figure 4:
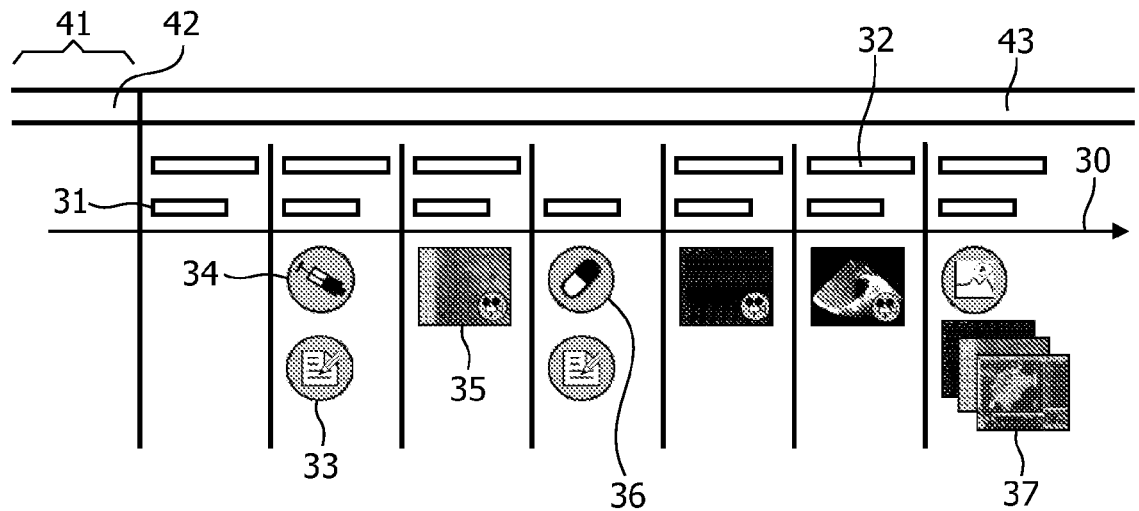
Figure 5:
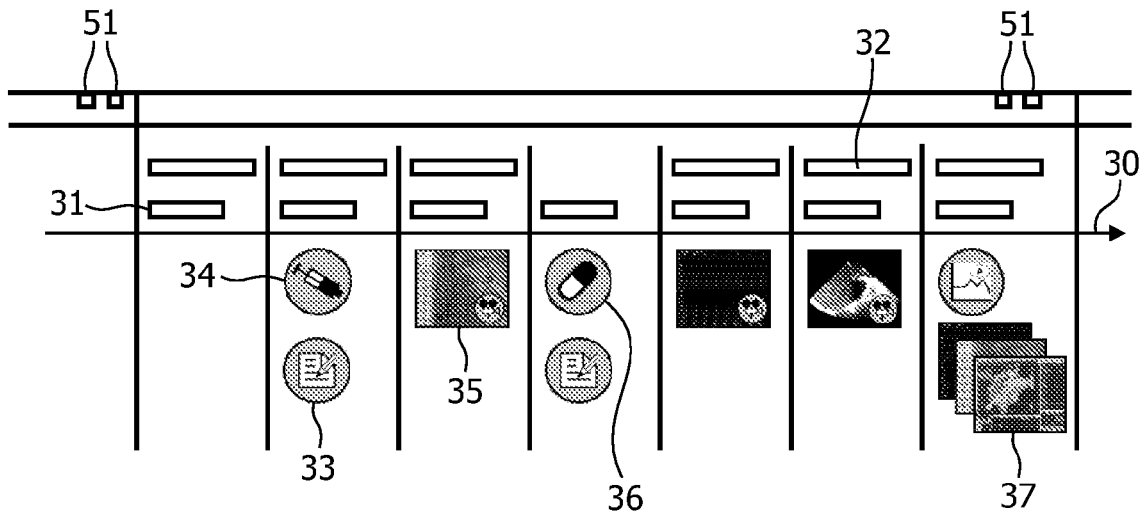

FIGS. 3-5 show exemplary timelines 30 as may be displayed according to the invention. Items 33-37 are sequentially ordered along the timeline 30. In the timeline 30 the following items may be shown/saved:

medications, as entered in CIS (cardiology information systems) currently with link to inventory management and billing materials (as entered in CIS currently with link to inventory management and billing)

snapshots (screenshots of e.g. 3D mapping systems, automatically placed in timeline)

X-ray runs (automatically when a run is made)

EP recording data and runs (automatically and/ or manually)

ablation data (automatically when ablating)

hemodynamic data

Data from programmers (measurements, settings etc.)

Time labels 31 may provide information about the moment in time that is represented by a particular part or section of the time line 30. Text labels 32 may provide additional information about a particular sub period of the interventional procedure. For example, a text label 32 may indicate the main event occurring in a sub period (start, place catheters, XA run 1, flutter, punction, ablation, . . .).

Viewing the timeline is very flexible, which is advantageous since lots of information is present but probably not all information need to be shown. A few specifications for respective embodiments:

Icons and pictures 33-37 are used to create a good overview

Events can be created automatically

Events can be entered manually (and will appear in the timeline 30)

Events can be edited or deleted

Multiple events can be merged into one (item 37)

Events can be hidden

Events can be labeled automatically (e.g. automatically created events), but also manually By clicking on an event the saved data is shown By clicking on data coming from another system 16 (e.g. recording run) the data will be opened and shown on the corresponding system 16

By clicking on data in the timeline 30 after the procedure the data should be opened in the viewer within a PACS system the timeline is "connected" to (e.g. recording viewer).

Other options for the system according to the invention in specific embodiments:

It may be possible to run the timeline as a thin client on different applications Depending on the user logged on to the system, different views on the timeline can be configured.

Some steps (which cannot be forgotten) can already be present in the timeline to guide the user through the procedure.

In FIG. 4, the timeline 30 is extended with information from the "Pre holding" area 41. Similarly, the timeline may continue during the direct care after the procedure; the "After care". A clear distinction between these different phases will be present. Such a distinction may, e.g., be provided using a title bar 42, 43, describing the phase. Preferably, the different phases are labeled and the current phase is distinctly displayed, e.g. highlighted or colored.

Because the timeline can be quite long, especially when including a 'pre holding' and an 'after care' area. Therefore, the embodiment of FIG. 5 provides the possibility to enlarge and minimize phases, by clicking or selecting user interface elements 51 provided for that purpose.

Figure 6:
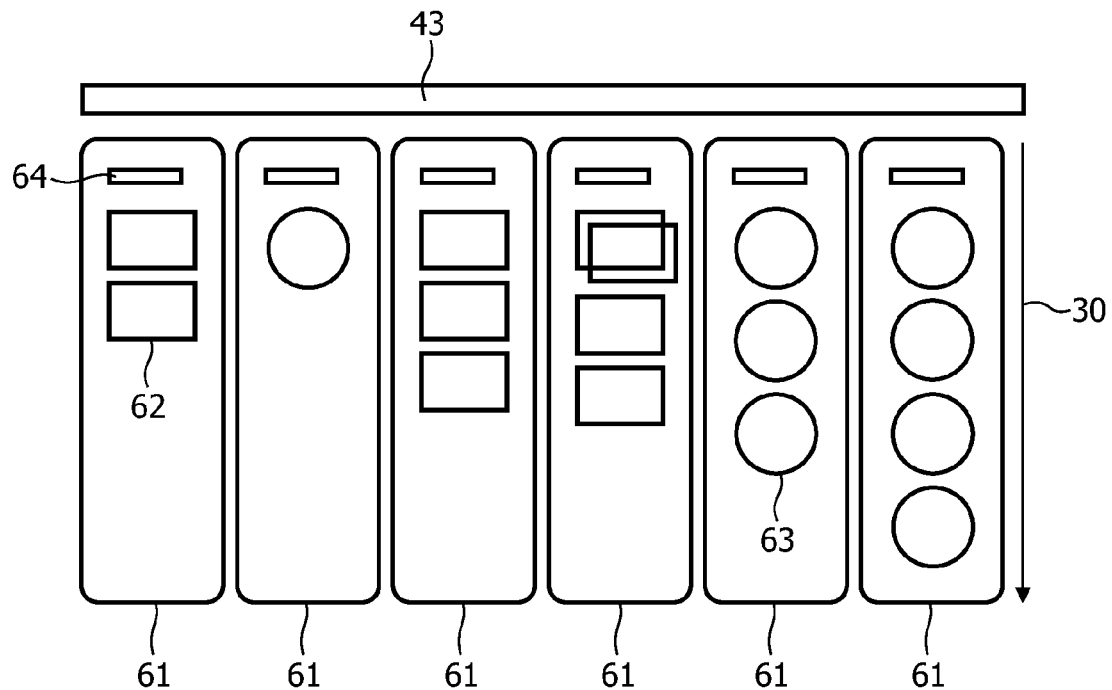
FIGS. 6 and 7 show categorized timelines as may be displayed according to the invention.
Figure 7:
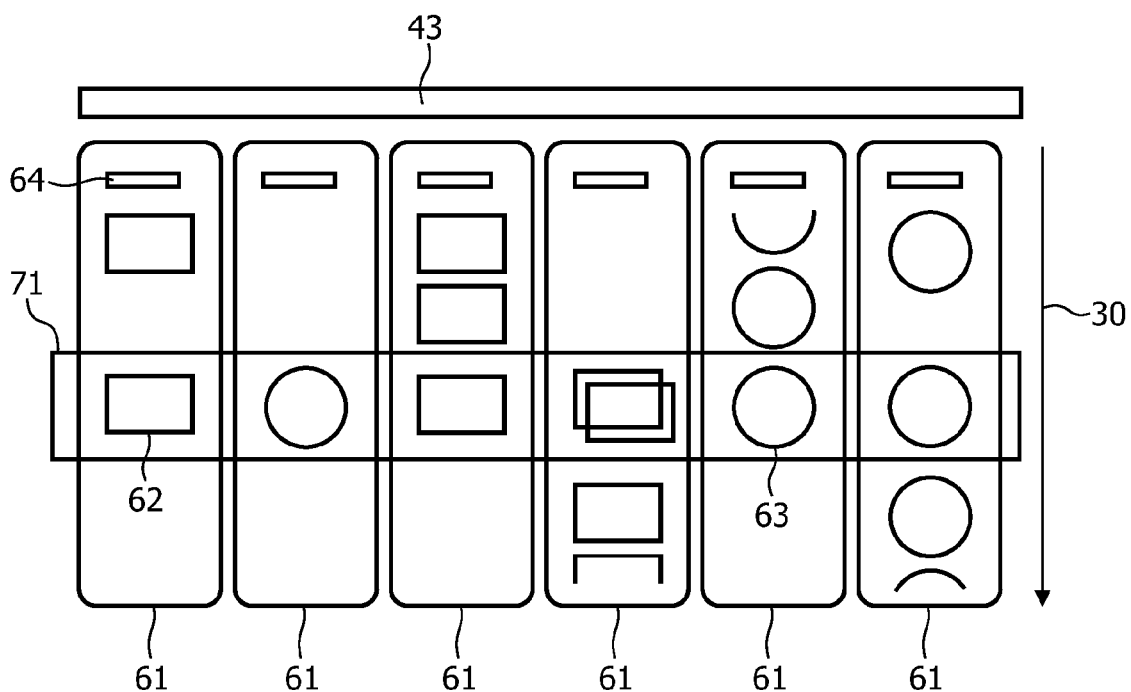

FIGS. 6 and 7 show categorized timelines as may be displayed according to the invention. The time line 30 may have various viewing possibilities. Besides the visualization shown above, there is optionally the possibility to show the data per category as well. This may, for example be done like shown in FIGS. 6 and 7. FIG. 6 shows a title bar 43, a time line 30 and category columns 61. Items 62, 63 are placed in the category column 61. In FIG. 6, the items 62 are placed in sequential order, with the earliest item at the top and the latest item on the bottom. The time scale is not necessarily linear and may vary from column 61 to column 61. Preferably, columns 61 are labeled using text labels 64.

The user can search for data per category, e.g. X-ray, snapshots or medications. This is a different way of looking at the data. Instead of looking for a certain moment in time, the user now starts with a certain kind of data and then searches within this data for the right item. If the user clicks on an item 62, 63 all items 62, 63 that were saved at that moment in time will be placed next to each other (FIG. 7), so the user has an overview of the information created at that time. FIG. 7 shows a time window 71, highlighting all items that relate to the same time or time period as the selected item 62, 63. Other items are moved up or down to keep the items within a column 61 in time sequential order. Some items, lying outside the time window 71 may be shifted partly or completely out of view.

Figure 8:
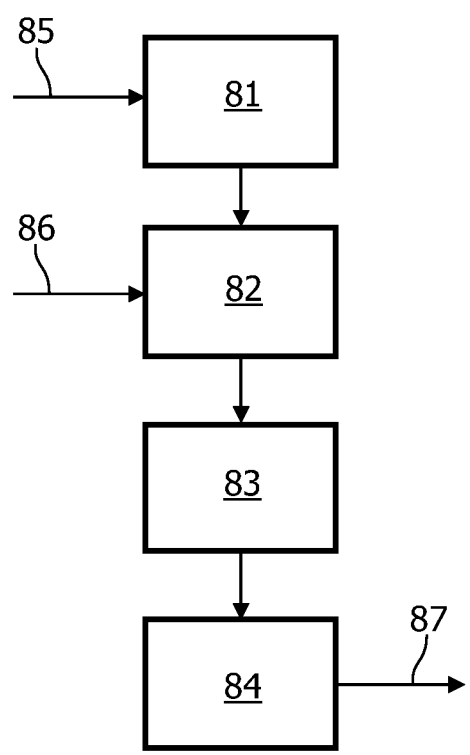
FIG. 8 shows a flow diagram of a method according to the invention.

FIG. 8 shows a flow diagram of a method according to the invention. The method uses data elements 85 elating to events in an interventional procedure as input and provides a timeline 87 as output. Many exemplary embodiments of the timeline 87 have been discussed above. In a receiving step 81 the data elements 85 from at least two, preferably more, systems used in the interventional procedure are received. In timestamp step 82, the time of receipt 86 of the data elements 85 is registered. In a storage step 83, the input data (data elements 85 and times of receipt 86) is stored in a database. Items in the database relate to events occurring during the interventional procedure. An item comprises data elements 85 concerning the event and time of receipt 86 of said data elements 85. In timeline generating step 84, the stored items are processed to generate a timeline 87 as described above. In this step 84, the items are placed sequentially along the timeline. The timeline 87 is provided as output, e.g., by displaying it on a display screen, or sending timeline data 87 to another system or device. The method may completely be performed in real-time during the interventional procedure, such that items occur on the timeline while their corresponding events are occurring. Alternatively, the timeline generating step 84 is performed at a later stage, after the interventional procedure has been completed. Preferably, the system performing the method is capable of showing real-time timelines as well as timelines concerning past procedures.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for collecting data elements relating to events in an interventional procedure that penetrates a body, the system comprising:
   a receiver configured to receive the data elements from a plurality of input systems configured to penetrate the body surgically with electromagnetic radiation in an electrophysiology interventional procedure or to penetrate the body surgically with the electromagnetic radiation and through a natural entry to reach at least one body cavity wherein the body cavity includes at least one of lungs, womb, bladder, intestines and stomach, wherein the natural entry is selected from one of the anus, the nose and the mouth; and
   wherein the electromagnetic radiation is selected from X-rays, lasers, gamma-rays and ultraviolet light, each data element corresponding to an event inside the penetrated body;
   a clock for registering a time of receipt of each of the data elements,
   a memory configured to store the data element and the corresponding time of receipt; and
   a display configured to display representations of the data elements sequentially along a timeline in accordance with the respective times of receipt,
   wherein the representations are icons illustrative of an event type of the events.

2. The system as claimed in claim 1, wherein the receiver is further configured to receive a manually provided data elements.

3. The system as claimed in claim 1, wherein the display is further configured to display the representations of the data elements when the corresponding event type is selected.

4. The system as claimed in claim 3, further comprising a transmitter configured to, when the event type is selected, send the data elements relating to the corresponding event to another system.

5. The system as claimed in claim 1, wherein the display is further configured to display the representations such that the events corresponding to the same event type are grouped.

6. The system of claim 1, wherein the display is further configured:
   to group related representations of the data elements corresponding to a same event type;
   to display the grouped related representations in category columns in a time sequential order, with an earliest representation at a top and a latest representation on a bottom of a category column; and
   to move the related representations in each of the category columns up or down so that representations from different category columns stored within a time period are aligned.

7. The system of claim 6, wherein the display is further configured to display a window around the aligned representations from the different category columns.

8. A method for collecting data elements relating to events in an interventional procedure that penetrates the body, the method comprising the acts of:
   receiving the data elements from a plurality of input systems configured to penetrate the body surgically with electromagnetic radiation in an electrophysiology interventional procedure or to penetrate the body surgically with the electromagnetic radiation, and through a natural entry to reach at least one body cavity, wherein the body cavity includes at least one of lungs, womb, bladder, intestines and stomach, wherein the natural entry is selected from one of the anus, the nose and the mouth; and wherein the electromagnetic radiation is selected from X-rays, lasers, gamma-rays and ultraviolet light, each data element corresponding to an event inside the penetrated body;
   registering a time of receipt of each of the data elements;
   storing data element and a corresponding time of receipt; and
   displaying representations of the data elements sequentially along a timeline in accordance with the respective times of receipt, the representations being icons illustrative of an event type of the events.

9. The method of claim 8, further comprising the acts of:
   grouping related representations of the data elements corresponding to a same event type;
   displaying the grouped related representations in category columns in a time sequential order, with an earliest representation at a top and a latest representation on a bottom of a category column; and
   moving the related representations in each of the category columns up or down so that representations from different category columns stored within a time period are aligned.

10. The system of claim 9, further comprising the act of displaying a window around the aligned representations from the different category columns.

11. A non-transitory computer readable medium comprising a computer program product, when executed by a processor the program being operative to perform a method for collecting data elements relating to events in an interventional procedure, the method comprising acts of:
   receiving the data elements from a plurality of input systems configured to penetrate the body surgically with electromagnetic radiation in an electrophysiology interventional procedure or to penetrate the body surgically with the electromagnetic radiation and through a natural entry to reach at least one body cavity wherein the body cavity includes at least one of lungs, womb, bladder, intestines and stomach, wherein the natural entry is selected from one of the anus, the nose and the mouth; and wherein the electromagnetic radiation is selected from X-rays, lasers, gamma-rays and ultraviolet light, each data element corresponding to an event inside the penetrated body;
   registering a time of receipt of each of the data elements;
   storing the data element and a corresponding time of receipt; and
   displaying representations of the data elements sequentially along a timeline in accordance with the respective times of receipt, the representations being icons illustrative of an event type of the events.

* * * * *